US009351869B2

(12) United States Patent
Knott et al.

(10) Patent No.: US 9,351,869 B2
(45) Date of Patent: May 31, 2016

(54) TEMPERATURE CONTROL DEVICE FOR FLUID-BASED HYPER/HYPOTHERMIA SYSTEMS

(75) Inventors: Erwin Knott, Poing (DE); Manfred Fronhöfer, München (DE)

(73) Assignee: Sorin Group Deutschland GmbH, Munich (DE)

(*) Notice: Subject to any disclaimer, the term of this patent is extended or adjusted under 35 U.S.C. 154(b) by 354 days.

(21) Appl. No.: 13/441,603

(22) Filed: Apr. 6, 2012

(65) Prior Publication Data

US 2012/0259394 A1    Oct. 11, 2012

(30) Foreign Application Priority Data

Apr. 8, 2011 (DE) .................... 10 2011 016 508

(51) Int. Cl.
*A61F 7/02* (2006.01)
*A61F 7/00* (2006.01)
*A61M 1/36* (2006.01)

(52) U.S. Cl.
CPC .............. *A61F 7/0085* (2013.01); *A61M 1/369* (2013.01); *A61M 2205/3368* (2013.01); *A61M 2205/36* (2013.01); *A61M 2205/82* (2013.01); *A61M 2205/8206* (2013.01)

(58) Field of Classification Search
CPC ...................... A61B 18/02; A61B 2018/00011; A61B 2018/0041; A61B 2018/00744; A61B 2018/00714; A61B 2018/046; A61B 2018/048; A61B 18/04; A61F 7/0053; A61F 7/0085; A61F 2007/0056; A61F 2007/008; A61F 7/0097; A61M 2205/82; A61M 2205/8206; A61M 2205/3368; A61M 2205/36; A61M 1/369

USPC ..................... 607/104; 606/20, 29, 31, 34
See application file for complete search history.

(56) References Cited

U.S. PATENT DOCUMENTS

| 4,517,633 | A | | 5/1985 | Melcher | |
|---|---|---|---|---|---|
| 4,966,145 | A | * | 10/1990 | Kikumoto | A47C 7/74 165/46 |
| 5,019,076 | A | * | 5/1991 | Yamanashi | A61B 18/082 606/45 |
| 5,871,526 | A | * | 2/1999 | Gibbs | A61F 7/02 165/46 |
| 6,117,164 | A | | 9/2000 | Gildersleeve et al. | |

(Continued)

FOREIGN PATENT DOCUMENTS

DE          3883452 T2    8/1993
DE          69331840 T2   4/2002

(Continued)

OTHER PUBLICATIONS

International Preliminary Report on Patentability issued in PCT/US2012/056154, completed Aug. 13, 2013, 10 pages.

(Continued)

*Primary Examiner* — Michael Peffley
*Assistant Examiner* — Thomas Giuliani
(74) *Attorney, Agent, or Firm* — Faegre Baker Daniels LLP

(57) ABSTRACT

Temperature control device for use in fluid-based hyper/hypothermia systems, comprising a connection unit for connecting the device to a local power network, and a fluid temperature control unit for heating or cooling a fluid. The device includes a power supply unit, by which electrical consuming components of the fluid temperature control unit are supplied with power, and which effects supply of the electrical consuming components with direct current.

10 Claims, 2 Drawing Sheets

(56) References Cited

U.S. PATENT DOCUMENTS

| | | | |
|---|---|---|---|
| 6,156,007 A | 12/2000 | Ash | |
| 6,175,688 B1* | 1/2001 | Cassidy et al. | 392/470 |
| 6,581,403 B2 | 6/2003 | Whitebook et al. | |
| 6,635,076 B1 | 10/2003 | Ginsburg | |
| 6,891,136 B2* | 5/2005 | Bikovsky et al. | 219/528 |
| 6,939,347 B2 | 9/2005 | Thompson | |
| 7,176,419 B2 | 2/2007 | Ellis et al. | |
| 7,220,260 B2* | 5/2007 | Fleming et al. | 606/39 |
| 2003/0060864 A1 | 3/2003 | Whitebook et al. | |
| 2004/0068310 A1 | 4/2004 | Edelman | |
| 2004/0149711 A1* | 8/2004 | Wyatt | A61F 7/00 219/217 |
| 2004/0267340 A1* | 12/2004 | Cioanta | A61F 7/123 607/105 |
| 2007/0020142 A1 | 1/2007 | Federspiel et al. | |
| 2009/0056344 A1* | 3/2009 | Poch | A61M 1/369 62/3.3 |
| 2009/0069731 A1 | 3/2009 | Parish et al. | |
| 2010/0030306 A1* | 2/2010 | Edelman et al. | 607/104 |
| 2010/0106229 A1* | 4/2010 | Gammons et al. | 607/104 |
| 2010/0143192 A1 | 6/2010 | Myrick et al. | |
| 2012/0167879 A1* | 7/2012 | Bowman et al. | 128/201.22 |
| 2012/0259394 A1 | 10/2012 | Knott et al. | |
| 2013/0079763 A1* | 3/2013 | Heckel | A61B 18/1206 606/33 |
| 2013/0331739 A1* | 12/2013 | Gertner | A61B 5/412 601/2 |
| 2014/0121734 A1 | 5/2014 | Knott et al. | |

FOREIGN PATENT DOCUMENTS

| | | |
|---|---|---|
| DE | 69634572 T2 | 2/2006 |
| EP | 1267958 A2 | 1/2003 |
| EP | 1970080 A1 | 9/2008 |
| JP | 2005514085 A | 5/2005 |
| WO | WO0172352 A2 | 10/2001 |
| WO | WO2006063080 A1 | 6/2006 |

OTHER PUBLICATIONS

International Search Report and Written Opinion issued in PCT/US2012/056154, mailed Jun. 26, 2012, 9 pages.

Netzteil (English: Power Supply), downloaded from German Wikipedia on Apr. 5, 2011, with English Wikipedia translation downloaded on Dec. 23, 2013.

Schaltnetzteil (English: Switching Power Supply), downloaded from German Wikipedia on Mar. 30, 2011, with English Wikipedia translation downloaded on Dec. 23, 2013, 13 pages.

* cited by examiner

TEMPERATURE CONTROL DEVICE FOR FLUID-BASED HYPER/HYPOTHERMIA SYSTEMS

CROSS-REFERENCE TO RELATED APPLICATION

This application claims priority to German Application No. 10 2011 016 508.8, filed Apr. 8, 2011, which is herein incorporated by reference in its entirety.

TECHNICAL FIELD

The invention relates to a temperature control device for use in fluid-based hyper/hypothermia systems.

BACKGROUND

A fluid-based hyper/hypothermia system is disclosed, for example, in DE 696 34 572 T2. Fluid-based hyper/hypothermia systems that use a temperature-controlled fluid to raise the temperature of a human or animal body, body part or organ to above the normal core body temperature or to lower it to below the normal core body temperature require a temperature control device that provides a temperature-controlled fluid to accomplish the desired change in body temperature. The temperature of the fluid must be controlled in the temperature control device in accordance with the quantity of heat to be supplied to or removed from the body. The fluid, for example, must be heated or cooled and then maintained at a predetermined temperature.

SUMMARY

In order to heat or cool the fluid in a temperature control device, energy is required that is provided as a general rule by the local power network. Thus, a conventional temperature control device comprises a power supply which allows the temperature control device to be connected to the local power network. Both the power supply as well as numerous individual electrical consuming components of the temperature control device must be adapted to the local power network. Since there are different local power networks in different regions of the world, the region of the world in which the temperature control device is ultimately supposed to be used and the specifications of the local power network according to which the power supply of the temperature control device and the temperature control device itself have to be configured must, with a considerable amount of effort, always be taken into consideration when constructing a temperature control device for hyper/hypothermia applications.

Various embodiments of the invention simplify the construction of a temperature control device and provide a temperature control device for hyper/hypothermia systems that can be used in different regions of the world. This aim is achieved by a temperature control device for use in fluid-based hyper/hypothermia systems, comprising: a connection unit for connecting the device to a local power network; and a fluid temperature control unit for heating or cooling a fluid including a power supply unit that supplies electrical consuming components of the fluid temperature control unit with power, and supplies the electrical consuming components with direct current.

DETAILED DESCRIPTION

Figure 1:
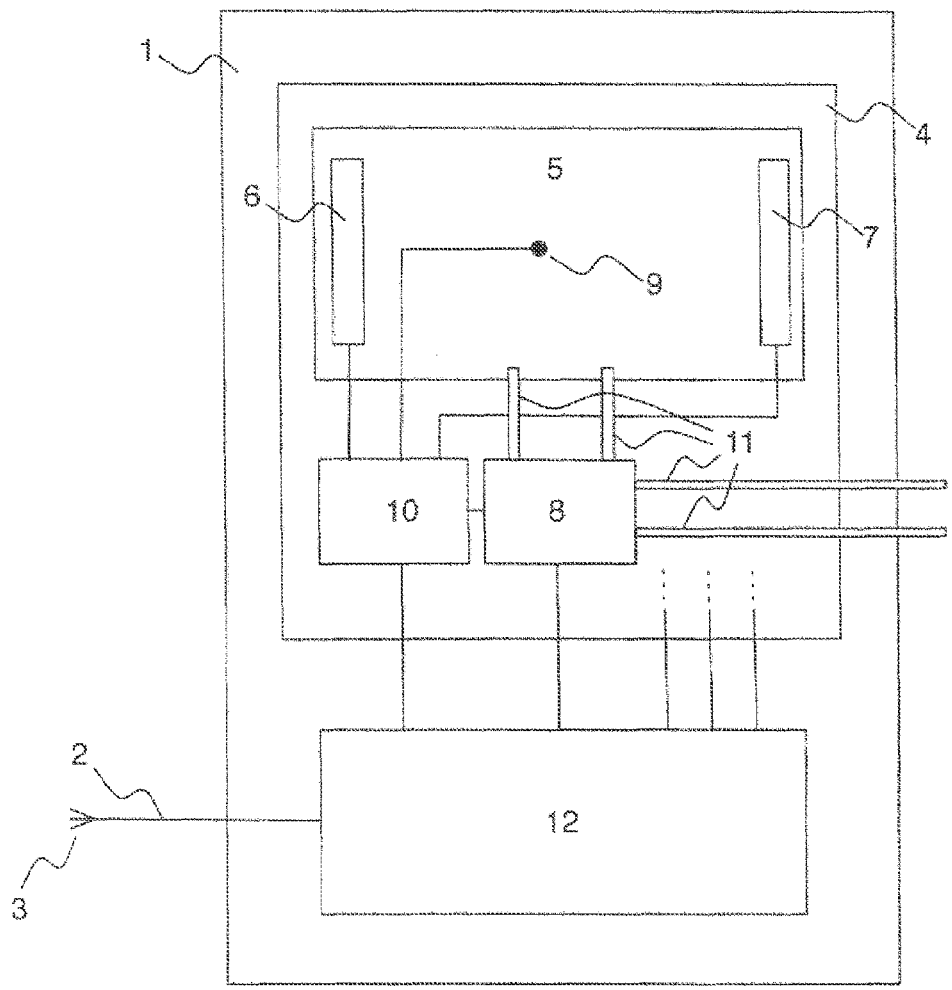
FIG. 1 shows an embodiment of a temperature control device according to the invention.

FIG. 1 shows a temperature control device 1 for use in a fluid-based hyperthermia or hypothermia system, according to embodiments of the invention. As shown in FIG. 1, the control device 1 includes a connection unit 2 for connecting the device to a local power network 3. In Germany, for example, the local power network is a general alternating current (AC) network of 220/380 V at 50 Hz. In Japan, for example, the local power network is an AC network of 100 V at, for example, 60 Hz. And in the United States, for example, the local power network is an AC network of 120 V at 60 Hz. These differences, and in particular the differences in frequency of the local power networks, lead to differences in the leakage currents which result from the change of the connected alternating current over time. For medical-technical systems in a surgical environment, the effects of electrical leakage currents, in the case for example of open heart surgeries, must remain minimal. To minimize these leakage currents, the electric lines in conventional temperature control devices must have certain insulations. This leads to increased material costs since, in particular, the insulation can age and must then be replaced if the guidelines with respect to the leakage currents are no longer met.

The temperature control device, according to the illustrative embodiments of the invention, is connected to the power network 3 via the connection unit 2 and can draw the power required to control the temperature of the fluid from the power network.

The temperature control of the fluid is accomplished by means of a fluid temperature control unit 4 which includes the components required for heating or cooling the fluid. These normally include a fluid container 5, a heater 6, a cooler 7, a supply pump 8, a temperature sensor 9 and a temperature controller 10 (e.g., a microprocessor), each of which are shown in FIG. 1 merely in schematic form and as an example of the components of the fluid temperature control unit 4. In this embodiment, the supply pump 8 works, for example, with a direct current motor and the cooler 7 includes a direct current compressor. Also shown by way of an example are pipelines 11, via which the pump 8 removes the fluid from the fluid container 5 and conveys it to the outside such that it can be used in the hyper/hypothermia system, or via which the fluid is conveyed out of the hyper/hypothermia system back into the fluid container 5. The pump can also be provided in the hyper/hypothermia system such that it can be omitted from the fluid temperature control unit 4 of a temperature control device 1 as according to the invention. Depending on the hyper/hypothermia system in which the temperature control device 1 is used, other components, such as a stirrer for the fluid in the fluid container 5, may be added to (or omitted from) the fluid temperature control unit 4. According to various embodiments, each of the components shown in FIG. 1 may be of the type disclosed in DE 696 34 572 T2, which is hereby incorporated by reference in its entirety.

To supply power to the electrical consuming components, for example, the heater 6, the cooler 7, the supply pump 8 and the temperature controller 10, of the fluid temperature control unit of a temperature control device 1, a power supply unit 12 is provided according to the invention, via which all of the electrical consuming components of the fluid temperature control unit 4 are electrically supplied with constant connected loads irrespective of the local power network. According to embodiments of the invention, direct current is supplied, for example, with a supply voltage of 48 V and a power of up to 3.5 kW. Accordingly, the electrical consuming components of the fluid temperature control unit 4 are supplied via the power supply unit and are, thus, not directly connected to the power network 3. Thus, these components need not be designed for the local power network, but are instead all supplied with direct current by the power supply unit 12. Different electrical consuming components can thereby be supplied with different voltages/powers which are provided by the power supply unit 12 according to the invention. This is indicated in FIG. 1 by the connections between the power supply unit 12 and the fluid temperature control unit 4, which are dashed at one end. The power supply unit 12 thereby performs adaptation to the local power network and conversion to a power supply with constant connected loads.

The power supply unit thus performs any and all necessary conversions to adapt the temperature control device to the conditions of a local or regional power network. The adaptation to the local power network of the region in which the device is to be used is achieved by an appropriate design of the power supply unit, which, on the side facing the connection unit, must be designed for connection to the local power network, but on the side facing the fluid temperature control unit, a uniform power supply with direct current is ensured irrespective of the local power network.

The power supply unit may be any standard power supply (including, for example, switched-mode power supplies) that provides (as standard) one or more of the supply voltages required by the fluid temperature control unit, so that the temperature of the fluid can be controlled. In this way, the fluid temperature control unit is electrically separate from the local power network. As a result, an improved electrical decoupling of the fluid temperature control unit from the power network is achieved, which has a positive effect on use in hyper/hypothermia systems, since network feedback and leakage currents can be reduced. In view of the fact that medical-technical systems such as hyper/hypothermia systems are subject to particularly critical specifications, this decoupling of the fluid temperature control unit from the local power network that is achieved by the power supply unit is advantageous.

Supplying the electrical consuming components of the fluid temperature control unit with direct current enables more precise control during operation, since a precise power control for each individual electrical consuming component can take place, for example, with the aid of inverters. This is true not only for the heater/cooler of the fluid temperature control unit, but also for the pumps which are generally electromotively driven. Overall, the improved controllability of the temperature control device of the invention leads to a reduction of noise in a hyper/hypothermia treatment scenario.

Figure 2:
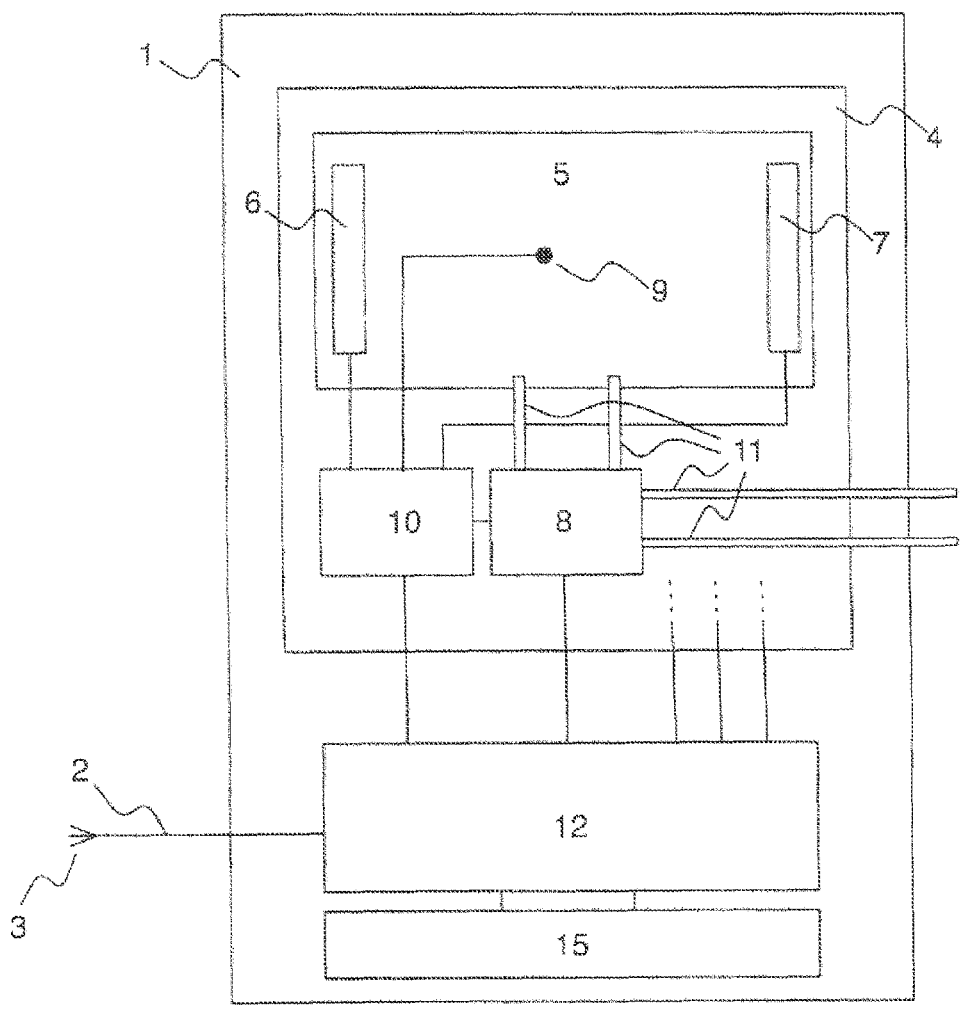
FIG. 2 shows a further embodiment of the temperature control device according to the invention.

FIG. 2 shows further embodiments of a temperature control device 1 according to the invention. As shown in FIG. 2, the control device 1 additionally includes a battery 15 for supplying the electrical consuming components of the fluid temperature control unit 4 with power. The battery 15 is connected to the power supply unit 12 and is charged by this unit when the supply of power occurs via the power network. In this way, the battery 15 can supply power to the power supply unit 12 to ensure delivery of a fail-safe supply of direct current to the electrical consuming components even where the local power network is subject to fluctuations or failure. Thus, designing the temperature control device with direct current electrical consuming components makes it possible to ensure the continuous operation of the temperature control device in a surgical environment.

We claim:

1. A temperature control device for use in fluid-based hyper/hypothermia systems, comprising:
   a connection unit for connecting the device to a local power network; and
   a fluid temperature control unit for heating or cooling a fluid in a surgical environment during heart surgery including a power supply unit that supplies electrical consuming components of the fluid temperature control unit with power, and is configured to supply the electrical consuming components with direct current and power of 3500 watts.

2. The temperature control device according to claim 1, wherein the power supply unit is a switched-mode power supply.

3. The temperature control device according to claim 1, wherein the electrical consuming components of the fluid temperature control unit comprise a direct current motor.

4. The temperature control device according to claim 1, wherein the electrical consuming components of the fluid temperature control unit comprise a direct current compressor.

5. The temperature control device according to claim 1, wherein the temperature control device comprises a battery for supplying the electrical consuming components of the fluid temperature control unit, the battery being connected to the power supply unit such as to be charged by the power supply unit or to supply the power supply unit.

6. A temperature control device for use in fluid-based hyper/hypothermia systems, comprising:
   a connection unit adapted for connecting the device to a local power network;
   a power supply unit adapted for receiving an alternating current power from the local power network and for converting the alternating current power from the local power network to a direct current power and configured to provide a supply voltage of 48 volts and power of 3500 watts; and
   a fluid temperature control unit for heating or cooling a fluid, the temperature control unit including a heater, a cooler, a supply pump, a temperature sensor, and a temperature controller;
   wherein each of the heater, the cooler, the supply pump, and the temperature controller are coupled to the power supply unit and are adapted to receive the direct current power.

7. The temperature control device according to claim 6, wherein the power supply unit is a switched-mode power supply.

8. The temperature control device according to claim 6, wherein the fluid temperature control unit comprises a direct current compressor.

9. The temperature control device according to claim 6, wherein the temperature control device comprises a battery connected to the power supply unit such as to be charged by the power supply unit or to supply the power supply unit.

10. A temperature control device for use in fluid-based hyper/hypothermia systems, comprising:
    a connection unit adapted for connecting the temperature control device to a local power network;
    a fluid temperature control unit including a pump and a cooler for cooling a fluid;
    a power supply unit connected to the connection unit and configured to receive an alternating current power from the local power network and convert the alternating current power from the local power network to direct current power and configured to provide power of 3500 watts, wherein the power supply unit is coupled to each of the pump and the cooler and configured to provide the direct current power to the pump and the cooler.

* * * * *